United States Patent [19]

Paulson et al.

[11] Patent Number: 5,061,680
[45] Date of Patent: Oct. 29, 1991

[54] SUPERCONDUCTING BIOMAGNETOMETER WITH REMOTE PICKUP COIL

[75] Inventors: Douglas N. Paulson, Del Mar; David S. Buchanan, San Diego; Eugene C. Hirschkoff, Leucadia; Mark S. DiIorio, San Diego; William C. Black, Jr., Del Mar, all of Calif.

[73] Assignee: Biomagnetic Technologies, Inc., San Diego, Calif.

[21] Appl. No.: 386,948

[22] Filed: Jul. 31, 1989

[51] Int. Cl.[5] .................. G01R 33/035; A61B 5/05; H01B 12/00; H01F 5/08
[52] U.S. Cl. .................. 505/1; 128/653 R; 324/248; 505/846
[58] Field of Search .................. 324/248, 201; 128/653 R, 731; 505/846

[56] References Cited

U.S. PATENT DOCUMENTS

| | | |
|---|---|---|
| 3,980,076 | 9/1976 | Wikswo, Jr. et al. .......... 324/248 X |
| 4,079,730 | 3/1978 | Wikswo, Jr. et al. .......... 324/201 X |
| 4,324,255 | 4/1982 | Barach et al. .................. 324/248 X |
| 4,793,355 | 12/1988 | Crum et al. .................... 324/248 X |
| 4,827,217 | 5/1989 | Paulson ............................ 324/248 |

FOREIGN PATENT DOCUMENTS

| | | | |
|---|---|---|---|
| 0246688 | 10/1988 | Japan | .................. 324/248 |
| 0016976 | 1/1989 | Japan | .................. 324/248 |
| 0078983 | 3/1990 | Japan | .................. 324/248 |

Primary Examiner—Gerard R. Strecker
Attorney, Agent, or Firm—Gregory O. Garmong

[57] ABSTRACT

A biomagnetometer has a magnetic pickup coil positioned remotely from the detector. The detector is made from a low-temperature superconductor, while the pickup coil and an electrical connector between the detector and the pickup coil are made of a high-temperature superconductor. Although the detector is maintained in a dewar at a sufficiently low temperature to reduce electronic noise, the pickup coil and the electrical connector need only be maintained at a temperature at which they are superconducting. In one approach, the detector is maintained at liquid helium temperature, and the pickup coil and electrical connector are cooled by liquid nitrogen. The resulting biomagnetometer permits the pickup coil to be moved and positioned easily, and to be changed readily.

20 Claims, 3 Drawing Sheets

SUPERCONDUCTING BIOMAGNETOMETER WITH REMOTE PICKUP COIL

BACKGROUND OF THE INVENTION

This invention relates to apparatus for the measurement of biomagnetic signals produced by the body, and, more particularly, to such apparatus in which the magnetic pickup coil may be positioned remotely from the detector.

The human body produces various kinds of energy that may be used to monitor the status and health of the body. Perhaps the best known of these types of energy is heat. Most healthy persons have a body temperature of about 98.6° F. A measured body temperature that is significantly higher usually indicates the presence of an infection or other deviation from normal good health. A simple medical instrument, the clinical thermometer, has long been available to measure body temperature.

Over 100 years ago, medical researchers learned that the body also produces electrical signals. Doctors today can recognize certain patterns of electrical signals that are indicative of good health, and other patterns that indicate disease or abnormality. The best known types of electrical signals are those from the heart and from the brain, and instruments have been developed that measure such signals. The electrocardiograph measures electrical signals associated with the heart, and the electroencephalograph measures the electrical signals associated with the brain. Such instruments have now become relatively common, and most hospitals have facilities wherein the electrical signals from the bodies of patients can be measured to determine certain types of possible disease or abnormality.

More recently, medical researchers have discovered that the body produces magnetic fields of a type completely different than the other types of energy emitted from the body, but which are associated with electrical signals within the body. The research on correlating magnetic fields with various states of health, disease and abnormality is underway, but sufficient information is available to demonstrate that certain emitted magnetic fields are associated with conditions such as epilepsy. Present medical studies are investigating the nature of the normal and abnormal magnetic fields of the brain, and seeking to correlate those fields with brain functions and patient health.

For example, if it were known that a particular abnormality, such as epilepsy, were associated with an abnormal magnetic field produced at a particular location in the brain, then it might be possible to detect the abnormality at an early stage, while it was treatable, and then apply other medical knowledge to chemically treat or surgically remove that precise portion of the brain with minimal side effects on the patient. Magnetic studies of the brain therefore offer the potential for understanding and treating some of the most crippling diseases and conditions known.

The biomagnetometer is an instrument that has been developed for measuring magnetic fields produced by the body, particularly the brain. The biomagnetometer is a larger, more complex instrument than the medical instruments mentioned earlier, primarily because the magnetic fields produced by the body are very small and difficult to measure. Typically, the strength of the magnetic field produced by the brain is about 0.000000001 Gauss, at a distance of 1-2 centimeters from the head. By comparison, the strength of the earth's magnetic field is about 0.5 Gauss, or about five hundred million times larger than the strength of the magnetic field of the brain, as measured externally to the head. Most electrical equipment also produces magnetic fields, in many cases much larger than that of the earth's field. It is apparent that, unless special precautions are taken, it is not possible to make magnetic measurements of the human body because the external influences such as the earth's magnetism and nearby apparatus can completely overwhelm and mask the magnetic fields from the body.

The biomagnetometer includes a magnetic pickup coil connected to a very sensitive detector for magnetic signals. The currently most widely used detector is a Superconducting QUantum Interference Device or SQUID, which, in combination with a superconducting pickup coil, is sufficiently sensitive to detect magnetic signals produced by the brain. (See, for example, U.S. Pat. Nos. 4,386,361 and 4,403,189, whose disclosures are incorporated by reference, for descriptions of two types of SQUIDs.) The detector, pickup coil, and their associated equipment require special operating conditions such as a cryogenic dewar, and cannot be placed into the body or attached directly to the surface of the body. The dewar is maintained at liquid helium temperature (about 4.2K), to maintain the SQUID detector, the pickup coil, and the electrical connection between them in the superconducting state because of the small electrical currents involved, and to reduce the electrical noise that might otherwise influence the SQUID detector.

The present biomagnetometer therefore includes a dewar structure in which the pickup coil, the SQUID detector, and the electrical interconnect are immersed. The dewar normally is constructed with a tail (see U.S. Pat. No. 4,773,952, whose disclosure is incorporated by reference, for a description of the construction of the dewar), which permits placement of the pickup coil in proximity with the head of the patient, typically about 2 centimeters away. Special electronics is provided to filter out external effects such as the earth's magnetic field and the magnetic fields of nearby electrical instruments. (For a description of such a device, see U.S. Pat. Nos. 3,980,076 and 4,079,730, whose disclosures are herein incorporated by reference.) The patient and detector can also be placed into a magnetically quiet enclosure that shields the patient and the detector from the external magnetic fields. (For a description of such an enclosure, see U.S. Pat. No. 3,557,777, whose disclosure is herein incorporated by reference.) With these special precautions, medical researchers and doctors can now make accurate, reliable measurements of the magnetic fields produced by the brain, and are studying the relationship of these fields with diseases and abnormalities.

The existing approach of enclosing the pickup coil and the SQUID detector in a liquid-helium dewar is acceptable in many circumstances. Nevertheless, it would be desirable to have another approach wherein the bulk could be reduced, to permit more flexibility in the use of the biomagnetometer. It would also be desirable to permit changes in the pickup coil configuration without removing the coil from the dewar, which necessitates a restabilization and recalibration of the system when the new coil is immersed back into the dewar. The present invention fulfills these needs, and further provides related advantages.

SUMMARY OF THE INVENTION

The present invention provides a construction for a biomagnetometer having a magnetic pickup coil that is structurally remote from the detector. The pickup coil or, in the usual case, array of pickup coils, is much more easily manipulated into place adjacent a subject, because it is held in a smaller container than was previously possible. In the new approach, the pickup coil may be placed closer to the subject, and thence the source of the magnetic field, than possible with the prior approach. In one embodiment, the pickup coil is disconnectable from the detector, so that the type and configuration of pickup coil or array of pickup coils is readily changed by disconnecting one unit and connecting a second unit, thereby permitting optimization of the array configuration for a particular measurement. It is not necessary to cause a major thermal interruption to the detector during the course of the changeover, a significant advantage.

In accordance with the invention, a biomagnetometer comprises a magnetic pickup coil formed of a material that is superconducting at a temperature less than its superconducting transition temperature; a detector formed of a material that is superconducting at a temperature less than its superconducting transition temperature; and an electrical conductor connected at one end to the pickup coil and at the other end to the detector, the conductor being formed, for at least a portion of its length, of a material having a superconducting transition temperature of greater than the boiling point of liquid nitrogen. In this aspect of the invention, the pickup coil and the detector are formed of materials that have superconducting transition temperatures ($T_c$) either above or below the boiling point of liquid nitrogen, but the conductor has a $T_c$ above the boiling point of liquid nitrogen.

More specifically in respect to a preferred embodiment of the invention, but still in accordance with the invention, a biomagnetometer comprises a magnetic pickup coil formed of a material having a superconducting transition temperature of greater than 77K; a first container that contains the pickup coil, the first container maintaining the pickup coil at a temperature at which it is superconducting; a detector formed of a material that is superconducting at a temperature less than its superconducting transition temperature; a second container that contains the detector, the second container maintaining the detector at a temperature at which it is superconducting; and a cable extending from the pickup coil in the first container to the detector in the second container, the cable including an electrical conductor connected at one end to the pickup coil and at the other end to the detector, the conductor being formed, for at least a portion of its length, of a material having a superconducting transition temperature of greater than 77K, and a third container that encloses the electrical conductor and extends the length of the cable, the third container maintaining the conductor at a temperature at which it is superconducting.

The invention also extends to a process for providing a biomagnetometer, that emphasizes the construction permitting a remote placement of the pickup coil. In accordance with this aspect of the invention, a process for providing a biomagnetometer comprises the steps of constructing a magnetic pickup coil of a material having a superconducting transition temperature of greater than 77K; constructing a detector of a material that is superconducting at a temperature less than its superconducting transition temperature; and constructing an electrical conductor between the pickup coil and the detector that is, at least for a portion of its length, made of a material having a superconducting transition temperature of greater than 77K, whereby the pickup coil may be placed remotely from the detector.

A key aspect of the present invention is the realization that the pickup coil and the detector are maintained at superconducting temperatures for different reasons, and providing a structure that permits the two components to be maintained at different superconducting temperatures. The structure having provision for two superconducting temperatures allows the pickup coil to be positioned remotely from the detector, which results in major advantages from the standpoint of the practical utilization of the biomagnetometer. By contrast, in existing biomagnetometers, the pickup coil, detector, and electrical interconnect are necessarily maintained at a single superconducting temperature below about 10K, and usually at liquid helium temperature, 4.2K.

In existing apparatus, the pickup coil and the electrical connector from the pickup coil to the detector are maintained at superconducting temperature because the currents flowing therethrough are very small and of a low frequency of 0-5 kilohertz, and even low electrical resistances in these elements would prevent the measurement of such small, low frequency magnetic fields. The detector is maintained at superconducting temperature in part for the same reason, to avoid electrical resistance, but also because thermally induced noise in the circuit should be maintained at a very low level. The detector must therefore be maintained at a temperature of less than about 10K, and usually is immersed in liquid helium or cooled by a sophisticated mechanical cooler. It has not been practical to place the pickup coil in a separate, remote container and have a superconducting electrical connector to the detector, because of the extreme difficulty in maintaining the electrical connector at the superconducting temperature of below 10K.

With the discovery of superconductors having superconducting transition temperatures above 77K, the biomagnetometer of the invention can be constructed with the pickup coil and the electrical connector of a material having a superconducting transition temperature above 77K, the boiling point of liquid nitrogen. The pickup coil may be remotely placed and maintained below its superconducting transition temperature, and the electrical connector may also be readily maintained below its superconducting transition temperature. That is, the pickup coil may easily be maintained at liquid nitrogen temperature or above, and the connector may be easily maintained at liquid nitrogen temperature or above, even over a long length of electrical connector, using containers cooled with liquid nitrogen and existing insulation techniques.

The detector may still be maintained at an acceptable operating temperature, which may be near absolute zero or at some higher temperature. The low noise, high temperature SQUIDs permit the detector to be operated at a higher temperature than 10K, and possibly even higher than 77K. Thus, both the magnetic pickup coils and the detector may be operated at relatively high temperature, and even at the same high temperature, but physically separated in the manner disclosed herein.

Thus, in a preferred approach the detector remains essentially stationary, and the pickup coil and electrical connector are readily moved about while remaining tethered to the detector. Since the detector always stays at its operating temperature, the electrical connector may be disconnected to replace the pickup coil with another design of pickup coil, without serious thermal interruption to the apparatus.

Other features and advantages of the invention will be apparent from the following more detailed description of the preferred embodiment, taken in conjunction with the accompaying drawings, which illustrate, by way of example, the principles of the invention.

DETAILED DESCRIPTION OF THE PREFERRED EMBODIMENT

Figure 1:
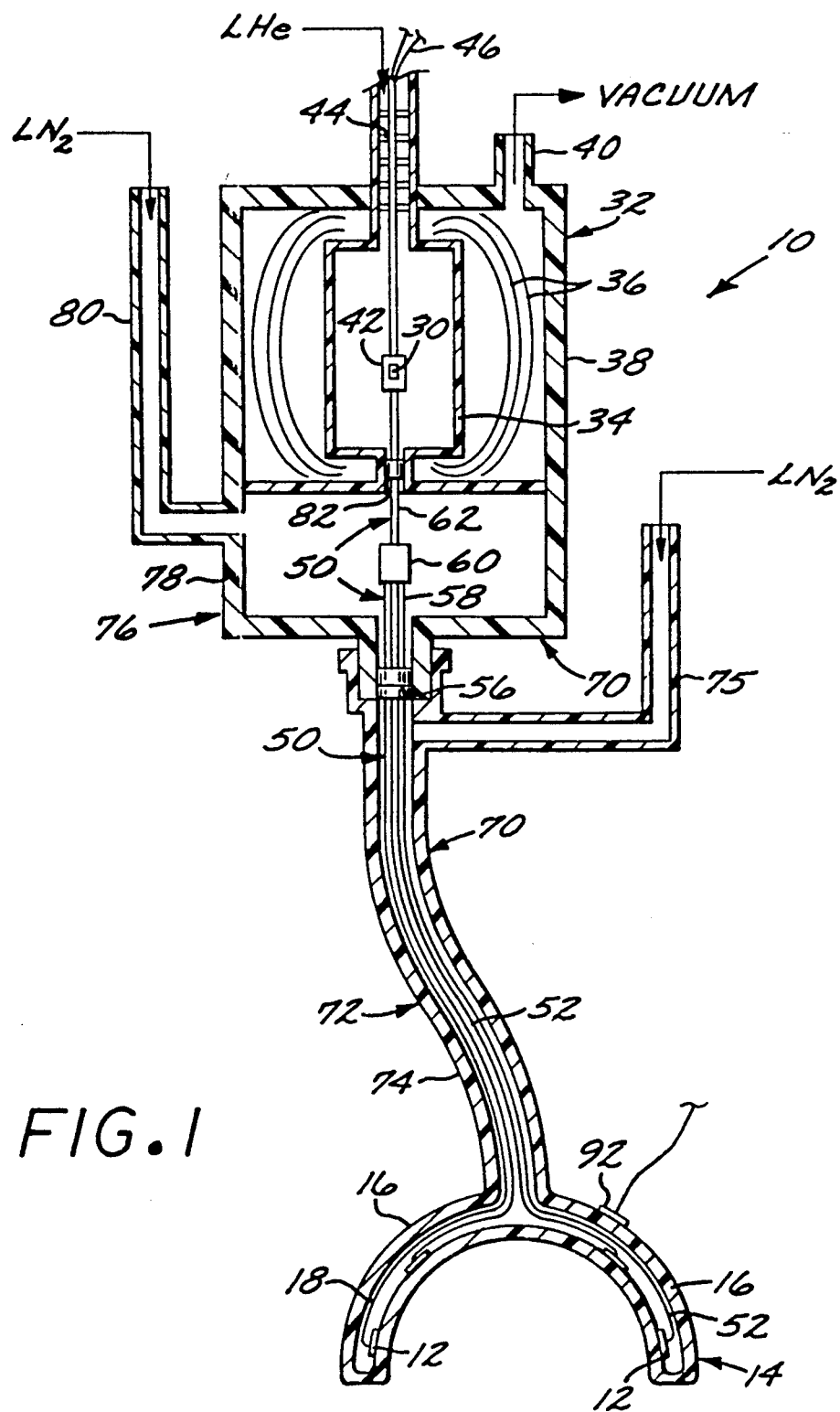
FIG. 1 is a side sectional view of an apparatus in accordance with the invention.

The preferred biomagnetometer 10 utilizing the present invention is illustrated in FIG. 1. The biomagnetometer 10 includes a pickup coil 12 in a first container 14. In normal operation, there will be multiple pickup coils 12 within the container 14. The pickup coil 12 is preferably formed of a material having a superconducting transition temperature of greater than 77K. The presently preferred material of construction of the pickup coil 10 is $YBa_2Cu_3O_{7-x}$, where x is typically about 0.1-0.2, depending upon the fabrication approach of the oxide. This material has been demonstrated to have a superconducting transition temperature of greater than 77K. Other materials having superconducting transition temperatures greater than 77K are also acceptable. Some examples include $Bi_2Ca_2Sr_2Cu_3O_{10}$ and $Tl_2Ba_2Ca_2Cu_3O_{10}$. As used herein, the "superconducting transition temperature" is the highest temperature at which the material becomes superconducting, in the absence of an applied magnetic field.

When small, low frequency magnetic fields are to be received by a pickup coil, the coil must be maintained in the superconducting state to permit the current generated by the small magnetic field to flow freely and not be dissipated as ohmic heating. It is not required that the pickup coil be maintained at a temperature near absolute zero, and therefore the construction of the pickup coil from "high temperature superconductors" having superconducting transition temperatures at or above 77K is acceptable. Construction of the pickup coil from high temperature superconductors is not required, and more conventional low-temperature superconductors (having a $T_c$ below 77K) may instead be used in a less preferred embodiment.

The container 14 is formed as an insulated vessel 16 having an interior volume 18 for containing liquid nitrogen or other liquefied gas as a coolant. The walls of the vessel 16 can be made of rigid materials such as fiberglass or insulating foam, a construction well known in the industry for making liquid nitrogen dewars. The walls of the vessel 16 can also be made of flexible materials such as corrugated stainless steel in the form of an elongated, double walled tube, or supported membranes such as plastics. Such flexible metal construction is well known in the industry for transfer tubes used to move liquid nitrogen. A thin membrane construction is known in the industry to protect against intense cold, as in aerospace applications. The walls of the vessel 16 can also be made of a composite construction, wherein part is rigid and part is flexible. With this approach, the portions of the walls of the vessel 16 adjacent the pickup coils 12 can be made of a thin rigid material such as fiberglass, and other portions could be made of a flexible material so that the container 14 could be reshaped to conform to the body of the subject. The insulated walls of the vessel 16 prevent discomfort from the cold for the human subject contacted with the surface of the container 14.

The preference in using materials for the coil 12 having superconducting transition temperatures greater than 77K is dictated by the design of the system. If the materials had lower superconducting transition temperatures, then a higher degree of insulation and a more powerful coolant than liquid nitrogen would be required. Experience has shown that achieving such lower temperatures in the container 14 is difficult, particularly if the walls 16 are flexible to permit the ability to reshape the container. The use of higher temperature superconductors allows liquid nitrogen cooling or even cooling with other liquefied gases or by mechanical means, without excessive insulation mass in the walls 16 of the container 14. Liquid nitrogen cooling is preferred, because liquid nitrogen is cheap, plentiful, and widely available in most hospitals and research facilities. If cooling below the boiling point of liquid nitrogen, 77K at 1 atmosphere pressure, is required, providing the cooling is more difficult. The design of flexible insulated components is also much more difficult.

A detector 30 is placed within a second container 32. The detector 30 is a highly sensitive detector of small electrical currents, and is preferably a superconducting quantum interference device (SQUID). The detector 30 is formed of a material that is superconducting at temperatures below its superconducting transition temperature.

The detector 30 is preferably cooled to a temperature of near to absolute zero, such as below about 10K, and most preferably to liquid helium temperature, 4.2K. The detector 30 should be operated in the superconducting state to prevent loss of current by ohmic heating. For some applications, it is preferably operated at a temperature close to absolute zero to reduce thermally induced noise in the detection circuit. Thus, for many applications and in particular for most biomagnetic applications, the detector 30 is operated near to absolute zero in order to reduce noise in the circuit. It is not sufficient for these applications to cool the detector just to a superconducting temperature, where that temperature is above about 30K, because thermally induced noise may overwhelm the detected signal.

In other applications, however, it is not necessary to maintain the detector near to absolute zero, but only below its superconducting transition temperature. SQUIDs have been fabricated from high temperature superconductors of the type discussed previously, an example being a SQUID made from $YBa_2Cu_3O_{7-x}$. These high temperature SQUID detectors have noise levels at high frequencies, when operated at temperatures approaching or above 77K and at high frequencies, substantially higher than those of SQUIDs operated at near absolute zero. The high temperature SQUIDs might be used where the magnetic signals to be measured are relatively large, as in magnetocardiographic measurements of the heart, for example. Low temperature SQUIDs, such as those made of niobium and operated near to absolute zero, might be used where the magnetic signals to be measured are relatively much smaller (and therefore more likely to be undetectable in the instrument noise of a high temperature SQUID), as in magnetoencephalographic measurements of the brain.

Thus, while in the preferred embodiment the SQUIDs are low temperature SQUIDs operating near absolute zero in liquid helium, the invention is not so restricted. The SQUIDs may be high temperature SQUIDs operated near, or above, 77K, where the instrument noise requirements permit. In either case, however, the SQUIDs are operated below their superconducting transition temperatures.

Returning to the discussion of the preferred embodiment shown in FIG. 1, to maintain the detector 30 at temperatures near absolute zero, the second container 32 has an interior insulated wall 34 that permits it to be filled with liquid helium or other appropriate liquefied gas having a boiling point near absolute zero. Around the insulated walls 34 are heat shields 36 and an exterior insulated wall 38. The walls 34 and 38 are made of fiberglass, are good thermal insulators, and are vacuum impermeable. A vacuum line 40 is provided to communicate with the space between the walls 34 and 38, so that a vacuum may be drawn in this volume. The detector 30 is mounted on a support 42, which in turn is suspended through an opening in the top of the container 32. Heat shields 44 and the use of nonconducting fiberglass in the support 42 insulate the detector 30 against heat loss through the opening. Wires 46 that act as electrical contacts from the detector 30 to external instrumentation extend along the length of the support 42. The combination of the walls 34 and 38, the heat shields 36 and 44, and the vacuum between the walls 34 and 38 permits the detector 30 to be maintained at a temperature near absolute zero without undue expenditure of liquid gas coolant. The construction of such dewar vessels is described in greater detail in U.S. Pat. No. 4,773,952, whose disclosure is incorporated by reference. Alternatively, the detector may be cooled by a mechanical cooler, such as the type disclosed in allowed U.S. patent application Ser. No. 07/187,016, now U.S Pat. No. 4,872,321, which disclosure is incorporated by reference.

The pickup coil 12 and the detector 30 are electrically connected by a lead system 50. The lead system 50 extends from the pickup coil 12 to the detector 30, to convey signals from the pickup coil 12 to the detector 30. A lead 52 connects directly to the pickup coil 12 and is external to the second container 32, but connects to the interior of the second container 32 at a connector 56. From the connector 56, another lead 58 extends to a junction block 60, and another lead 62 extends from the junction block 60 to the detector 30. These various leads pass through several temperature environments, which will be described subsequently.

The leads 52, 58, and 62, as well as any elements of the connector 56 and junction block 60 that might carry current, are made of a material having a superconducting transition temperature of greater than 77K, so that signals from the pickup coil 12 are conveyed to the detector 30 with no resistive loss in current, when these components are maintained in the superconducting state. The same $YBa_2Cu_3O_{-x}$ material used for the coil 12 is preferred for use in these elements, and the other high $T_c$ superconductors mentioned earlier are also operable. If there is more than one pickup coil, there is provided a lead system for each pickup coil.

A third container 70 encloses the lead system 50 and maintains it in the superconducting state. The container 70 includes several parts in the preferred embodiment illustrated in FIG. 1. The lead 52 that extends from the pickup coil 12 to the connector 56 passes through the interior of the first container 14 for a short distance, and then through the interior of an elongated tube. 72.

Figure 4:
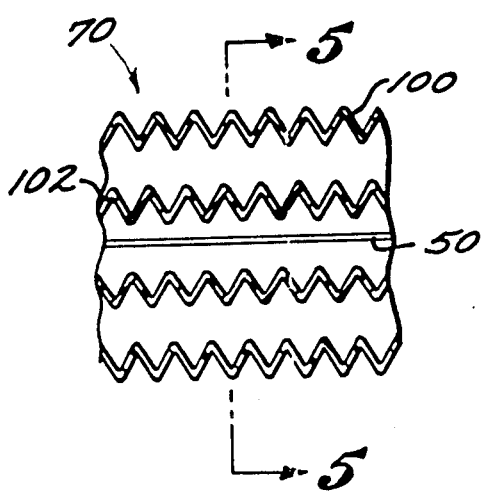
FIG. 4 is a side sectional view of a preferred flexible tube.
Figure 5:
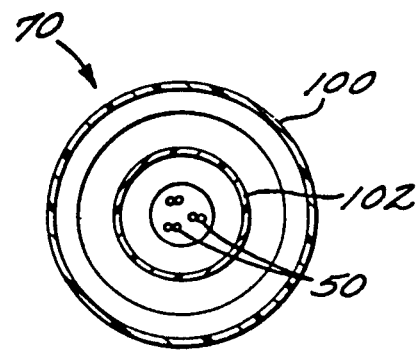
FIG. 5 is a cross sectional view of the tube of FIG. 4, taken along line 5—5.

The walls of the tube 72 are preferably, but not necessarily, flexible. FIGS. 4 and 5 illustrate the preferred construction of the container 70 in more detail. An outer wall 100 and an inner wall 102 are made of a corrugated stainless steel construction, essentially the same construction as the first container 14. Such a corrugated construction permits limited flexibility of the walls and bending of the container 70 along its long axis. It permits a greater degree of elastic bending than possible with the metal itself. Such flexible construction is known for fabricating flexible bellows used in transferring cryogenic fluids. In the preferred embodiment, the space between the outer wall 100 and the inner wall 102 is vacuum pumped to reduce conduction and convection heat loss. The space within the inner wall 102, holding the lead system 50, is filled with liquid gas, such as liquid nitrogen, to maintain the lead system 50 below its superconducting transition temperature during operation. The lead system may be formed from straight wires, if sufficiently flexible, or from the superconducting materials deposited upon a flexible substrate, such as a corrugated substrate, to achieve the same degree of flexibility as the outer and inner walls.

In the preferred approach, the interior of the tube 72 is continuous with, and communicates with, the interior of the first container 14. The tube 72 has a liquid gas fill tube 75 near its uppermost region, so that a liquid gas, most preferably liquid nitrogen, can be poured into the interior of the tube 72 and thence into the interior of the first container 14. In operation, the lead 52 is thereby maintained at a temperature below its superconducting transition temperature.

The lead 58, the junction block 60, and a lower portion of the lead 62 are contained within an insulated container 76 that is also part of the third container 70. The container 76 is attached to the underside of the second container 32, and has walls 78 formed of insulating fiberglass. A fill tube 80 permits liquid nitrogen to be poured into the interior of the container 76, so that the lead 58, the junction block 60, and the portion of the lead 62 within the container 76 are maintained at about 77K, below their superconducting transition temperatures. The upper portion of the lead 62 passes through a seal 82 into the interior of the second container 32, and is thence connected to the appropriate leads of the detector 30. The upper portion of the lead 62 is maintained at a temperature at which it is superconducting.

The connector 56 is provided between the leads 52 and 58, so that they may be readily disconnected from each other. While it would be acceptable to have the lead system 50 be a continuous length of superconducting material, it is desirable to provide the connector 56 so that the portion of the lead system 50 exterior to the containers 32 and 76 may be readily disconnected. By this approach, the entire pickup coil array may be removed and replaced with another array, without requiring that the detector 30 be warmed. The connector 56 may be a plug connector that seals against loss of liquid gas, an inductively coupled connector, or other acceptable type known in the field of cryogenics.

Figure 2A:
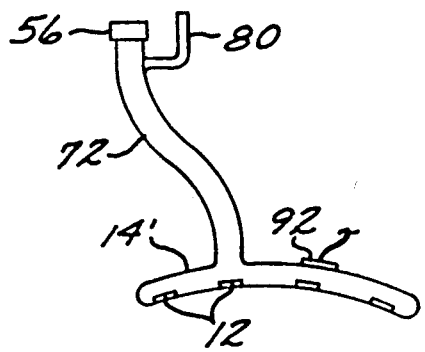
FIG. 2A-C are elevational views of several configurations of pickup coil and container operable with the present invention.
Figure 2B:
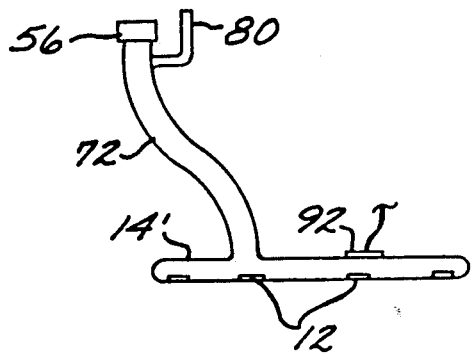
Figure 2C:
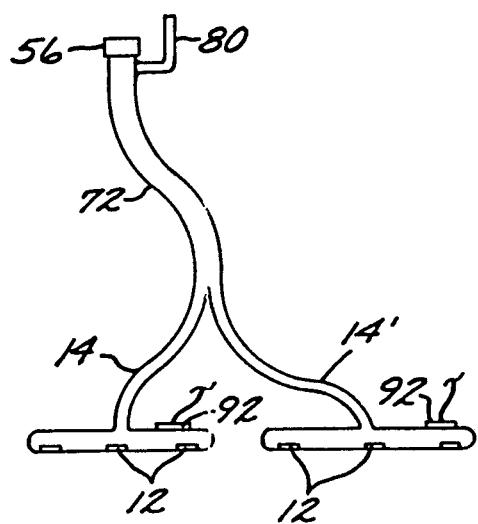

FIGS. 1, 2A, 2B, and 2C show some alternative configurations for an array of pickup coils 12 and the corresponding first container 14. In FIG. 1, the container 14 is configured to generally fir over the shull of a subject, somewhat like a cap, so that the array of coils 12 may be placed at many different locations relative to the brain of the subject. In FIG. 2A, the coils 12 and container 14' are in a gently curved form that could be placed against the body, as for example over the chest to sense magnetic fields produced by the heart. In FIG. 2B the coils 12 and container 14' are depicted in a flat form. FIG. 2C illustrates a form having two arrays of pickup coils 12 and 12', located respectively in two containers 14 and 14'. This configuration is suited for simultaneous measurements of different parts of the body, as, for example, the heart and the liver together or the brain and the heart together. In each case, there is provided a tube 72, fill tube 80, and one side of the connector 56.

It will be appreciated that these various configurations are presented as illustrative, and that custom configurations can be disigned and built using the techniques described herein. The important point is that, using the approach of the invention, the detector, which may require an operational temperature near absolute zero, is physically separated from the pickup coils, which need only be operated in the superconducting state and not necessarily near absolute zero, and connected with a lead system that also need only be operated in the superconducting state and not necessarily near absolute zero. Using high temperature superconductors having superconducting transition temperatures above 77K, the structure used to maintain the pickup coil and the lead system at or below the superconducting temperature is much simpler ans less bulky than the structure used to maintain the detector near absolute zero.

Figure 3:
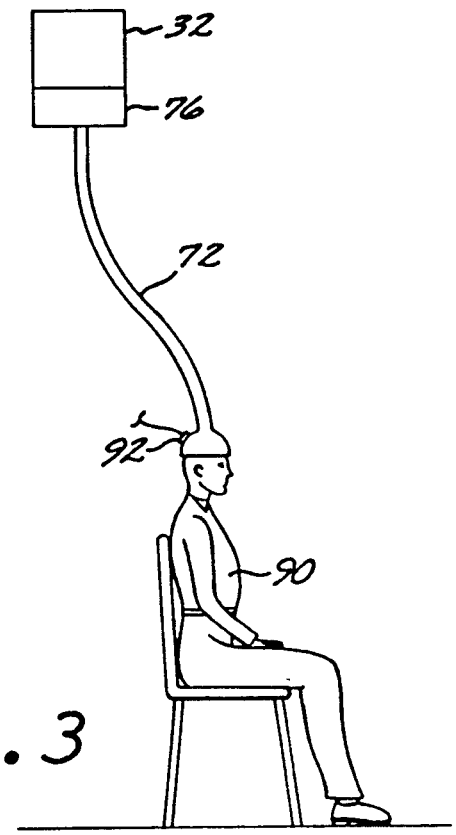
FIG. 3 is a perspective view of the operational arrangement of the apparatus of FIG. 1.

FIG. 3 illustrates the use of the preferred embodiment of the biomagnetometer 10, constructed according to the prior description and as shown in FIG. 1. A subject 90 sits in a chair, with the first container 14 on his or her head, and with an array of pickup coils therein positioned around the head. The second container 32 and container 76 are mounted above and some distance from the subject 90. The flexible tube 72 extends from the first container 14 to the containers 32 and 76.

This approach has important advantages over the prior approach, which is generally illustrated in FIG. 1 of U.S. Pat. No. 4,793,355, whose disclosure is incorporated by reference. In this prior approach, the pickup coils were necessarily located within the rigid, bulky dewar, and as a result could not be easily moved. The ability to arbitrarily position the pickup coils was also significantly limited. In the present approach, the pickup coils are located close to the body of the subject, resulting in higher resolution and lower noise. A large array of pickup coils 12 can be placed in proximity to the subject, and on all sides. This capability is expected to be great significance in advanced techniques now under development for correlating signals attained simultaneously from several pickup coils. The flexible tube 76 permits the subject to move around slightly, to avoid undue constraints that might cause unwanted signals in the brain. The use of a connector 56 between the tube 76 and the lead 58 allows the entire tube 76, array of pickup coils 12, and first container 14 to be disconnected and replaced with another unit without bringing the detector 30 to ambient temperature, which was impossible with the apparatus illustrated in the '355 patent.

The '355 patent discloses an approach for automatically tracking the position of the pickup coil and the subject. This approach is readily applied in conjunction with the present invention. Each of the first containers 12 shown in FIGS. 1–3 includes a position monitoring sensor 92 that is used in conjunction with the apparatus disclosed in the '355 patent to monitor the position of the coil array.

As the technology of superconductors advances, it is possible that materials which are superconducting at ambient temperature will be discovered. The present invention is operable with such materials used in the pickup coils 12 and the conducting portions of the lead system 50. In this instance, insulation for the containers that contain the lead system 50 is not required, except where the leads are brought to lower temperatures for connection with the detector 30.

Although a particular embodiment of the invention has been described in detail for purposes of illustration, various modifications may be made without departing from the spirit and scope of the invention, Accordingly, the invention is not to be limited except as by the appended claims.

What is claimed is:

1. A biomagnetometer, comprising:
magnetic pickup coil formed of a material having a superconducting transition temperature of greater than 77K, the pickup coil being adapted for picking up magnetic fields;
a first container that contains the pickup coil, the first container maintaining the pickup coil at a temperature at which it is superconducting;
a detector formed of a material that is superconducting at a temperature less than its superconducting transition temperature, the detector being adapted to detect small electrical currents;
a second container that contains the detector, the second container maintaining the detector at a temperature at which it is superconducting and being physically remote from the first container; and
a cable extending from the pickup coil in the first container to the detector in the second container, the cable including
an electrical conductor connected at one end to the pickup coil and at the other end to the detector and being adapted to convey electrical signals from the pickup coil to the detector, the conductor being formed, for at least a portion of its length, of a material having a superconducting transition temperature of greater than 77K,
a third container that encloses the electrical conductor and extends from the first container to the second container, the first, second, and third containers together enclosing and maintaining the pickup coil, the detector, and the cable at a temperature at which each is superconducting.

2. The biomagnetometer of claim 1, further including an electrical disconnect, made at least partially of a material that is superconducting at temperatures of greater than 77K, between the pickup coil and the detector.

3. The biomagnetometer of cliam 1, further including an inductively coupled electrical disconnect between the pickup coil and the detector.

4. The biomagnetometer of claim 1, wherein the electrical conductor is flexible.

5. The biomagnetometer of claim 1, wherein the third container is flexible.

6. The biomagnetometer of claim 1, wherein the detector is a superconducting quantum interference device.

7. The biomagnetometer of claim 1, wherein the detector is formed of a material having a superconducting transition temperature of less than 77K.

8. The biomagnetometer of claim 1, further including a first liquefied gas in the first container, the first liquefied gas having a boiling point of no less than 77K.

9. The biomagnetometer of claim 1, further including a second liquefied gas in the second container, the second liquefied gas having a boiling point of no greater than about 10K.

10. The biomagnetometer of claim 1, further including a third liquefied gas in the third container, the third liquefied gas having a boiling point of no less than 77K.

11. The biomagnetometer of claim 1, further including a second liquefied gas in the second container, the second liquefied gas being liquid 12. A biomagnetometer, comprising:
a magnetic pickup coil formed of a material that is superconducting at a temperature less than its superconducting transition temperature, the pickup coil being adapted for picking up magnetic fields;
a detector formed of a material that is superconducting at a temperature less than its superconducting transition temperature, the detector being adapted to detect small electrical currents, there being no container that encloses both the pickup coil and the detector; and
an electrical conductor connected at one end to the pickup coil and at the other end to the detector and being adapted to convey electrical signals from the pickup coil to the detector, the conductor being formed, for at least a portion of its length, of a matering having a superconducting transition temperature of greater than the boiling point of liquid nitrogen.

13. The biomagnetometer of claim 12, wherein the detector is a superconducting quantum interference device.

14. The biomagnetometer of claim 12, wherein the detector is made of niobium.

15. The biomagnetometer of claim 12, wherein the detector is made of a material having a superconducting transition temperature greater than the boiling point of liquid nitrogen.

16. The biomagnetometer of claim 12, wherein the pickup coil, the detector, and the electrical conductor are enclosed in insulated containers, the pickup coil and the detector being enclosed within different containers.

17. The biomagnetometer of claim 12, including a plurality of pickup coils, enclosed in at least two insulated containers.

18. The biomagnetometer of claim 12, wherein the electrical conductor is enclosed within an insulated, flexible container.

19. A biomagnetometer, comprising:
means for picking up a magnetic field and producing an electrical signal representative of the magnetic field, the means for picking up being operable when maintained at a temperature no greater than a first superconducting transition temperature;
first container means for containing the means for picking up and maintaining the means for picking up at a temperature no greater than the first superconducting transition temperature;
means for detecting a small electrical signal, the means for detecting being operable when maintained at a temperature no greater than a second superconducting transition temperature, the second superconducting transition temperature being no greater than the first superconducting transition temperature, the means for detecting being located outside of the first container means;
second container means for containing the means for detecting and for maintaining the means for detecting at a temperature no greater than the second superconducting transition temperature; and
means for transmitting the electrical signal from the means for picking up to the means for detecting without signal loss due to electrical resistance, and for permitting the first container means and the second container means to be physically separated from each other, the means for detecting thereby serving as a physically remote detector of the magnetic field sensed by the means for picking up.

20. The biomagnetometer of claim 19, wherein the means for transmitting further includes means for permitting the first container means and the second container means to be disconnected from each other without raising the temperature of the means for detecting above the second transition temperature.

* * * * *